United States Patent

Merk et al.

[11] 4,090,024
[45] May 16, 1978

[54] PROCESS FOR THE PRODUCTION OF SKATYLHYDANTOIN

[75] Inventors: Wolfgang Merk; Gerd Schreyer; Horst Weigel, all of Hanau, Germany

[73] Assignee: Deutsche Gold- und Silber-Scheideanstalt Vormals Roessler, Frankfurt, Germany

[21] Appl. No.: 765,425

[22] Filed: Feb. 3, 1977

[30] Foreign Application Priority Data

Feb. 7, 1976 Germany .............................. 2604842

[51] Int. Cl.² ........................................ C07D 403/06
[52] U.S. Cl. ................................................ 548/309
[58] Field of Search ...................... 548/309, 308, 313; 260/683.9, 690

[56] References Cited

PUBLICATIONS

Elks et al., J. Chem. Soc. (London), 1944, pp. 629–632.
Kittila, Dimethylformamide Chemical Uses, pp. 131–133, E. I. Du Pont de Nemours & Co., Inc., 1967.
Majima et al., Berichte, 1922, vol. 22, pp. 3859–3865.
Weygand, Organic Preparations, pp. 10–15, N.Y., Interscience, 1945.

*Primary Examiner*—Natalie Trousof
*Attorney, Agent, or Firm*—Cushman, Darby & Cushman

[57] ABSTRACT

Skatylhydantoin is prepared by hydrogenation of indolalhydantoin in the presence of a solvent and a hydrogenation catalyst wherein the solvent is a compound of the formula

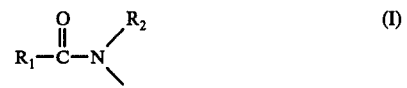

or

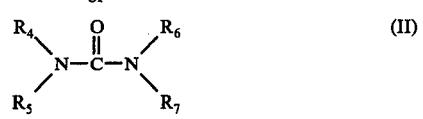

or a mixture of (I) and (II) and in which either $R_1$ to $R_3$ are hydrogen or $R_1$ is hydrogen or a straight or branched chain alkyl group with 1 to 6 carbon atoms and $R_2$ and $R_3$ each are straight or branched chain alkyl groups with 1 to 8 carbon atoms or an aryl group, or $R_2$ and $R_3$ together are a straight or branched chain alkylene group with 2 to 8 carbon atoms; or one of $R_2$ and $R_3$ is hydrogen and $R_1$ and $R_2$ or $R_3$ are joined to form a straight or branched chain alkylene group with 2 to 8 carbon atoms; and $R_4$ to $R_7$ each are straight or branched chain alkyl groups with 1 to 8 carbon atoms, an aryl group, an alkaryl group or an aralkyl group, or two of the substituents $R_4$ to $R_7$ together also are a straight or branched chain alkylene group with 2 to 8 carbon atoms, wherein the melting point of the solvent (or mixture of solvents) is below 50° C and a noble metal catalyst is used as the hydrogenation catalyst.

9 Claims, No Drawings

PROCESS FOR THE PRODUCTION OF SKATYLHYDANTOIN

BACKGROUND OF THE INVENTION

The object of the present invention is to develop a process for the production of skatylhydantoin by hydrogenation of indolalhydantoin in the presence of a solvent and a hydrogenation catalyst.

Skatylhydantoin is a valuable intermediate product for the production of D,L-tryptophane which can be obtained in good yields by the alkaline hydrolysis of the skatylhydantoin, see White U.S. Pat. No. 2,557,920.

It is already known to hydrogenate indolalhydantoin in caustic soda solution with sodium amalgam, see Majima Berichte Vol. 55 pages 3859–3865, particularly page 3863 (1922). However, only a yield of 68% of theory is produced thereby.

Also it is already known to catalytically hydrogenate indolalhydantoin in caustic soda in the presence of Raney nickel, see Elks, J. Chem. Soc., pages 629 to 632 (London, 1944). In this process, however, the catalyst must be added in an amount of 100 weight percent based on the weight of the material to be hydrogenated and a reaction time of 8 hours is required. If hydrogenation is carried out at 100° to 110° C and a hydrogen pressure of 50 atmospheres in 65 percent aqueous alcohol the reaction time is shortened to 2 hours. However, the yields only amount to 80% of theory, see J. Chem. Soc., loc. cit.

Finally it is also known to treat indolalhydantoin with aqueous ammonium sulfide and simultaneously hydrolyze the skatylhydantoin formed to D,L-tryptophane, see Livak, U.S. Pat. No. 2,435,399. However, the total yield amounts only to 56% of theory.

In all of the known processes, there were used aqueous or water containing solvents through which, particularly at temperatures above 60° C, besides the desired hydrogenation there also occurred saponification reaction which led to reductions in yield because of the formation of the hydroxy or keto analogues of D,L-tryptophane.

SUMMARY OF THE INVENTION

The invention is directed to a process for the production of skatylhydantoin by hydrogenation of indolalhydantoin in the presence of a hydrogenation catalyst wherein there is employed as a solvent at least one compound of the formula

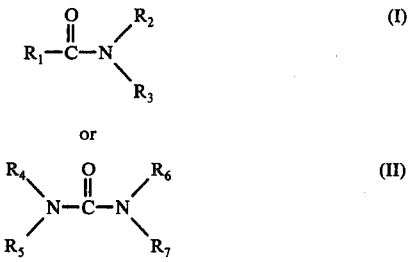

or a mixture of (I) and (II) and in which either $R_1$ to $R_3$ are hydrogen or $R_1$ is hydrogen or a straight or branched chain alkyl group with 1 to 6 carbon atoms and $R_2$ and $R_3$ each are straight or branched chain alkyl groups with 1 to 8 carbon atoms or an aryl group, or $R_2$ and $R_3$ together are a straight or branched chain alkylene group with 2 to 8 carbon atoms, or one of $R_2$ and $R_3$ is hydrogen and $R_1$ and $R_2$ or $R_2$ are joined to form a straight or branched chain alkylene group with 2 to 8 carbon atoms, and $R_4$ to $R_7$ each are straight or branched chain alkyl groups with 1 to 8 carbon atoms, an aryl group, an alkaryl group or an aralkyl group, or two of the substituents $R_4$ to $R_7$ together also are a straight or branched chain alkylene groups with 2 to 8 carbon atoms, wherein the melting point of the solvent, or mixture of solvents, is below 50° C and a noble metal catalyst is used as the hydrogenation catalyst.

A narrower group of starting compounds is that where $R_1$ to $R_3$ are all hydrogen or $R_1$ is hydrogen or alkyl with 1 to 3 carbon atoms and $R_2$ and $R_3$ are alkyl with 1 to 6 carbon atoms or $R_2$ and $R_3$ together are alkylene of 5 carbon atoms or one of $R_2$ and $R_3$ is hydrogen or methyl and $R_1$ and the other of $R_2$ and $R_3$ are joined to form an alkylene group of 3 to 4 carbon atoms, $R_4$ to $R_7$ are alkyl of 1 to 6 carbon atoms or one of $R_4$ to $R_7$ is phenyl and the remainder of $R_4$ to $R_7$ are alkyl of 1 to 6 carbon atoms.

A still narrower group of starting compounds is that where $R_1$ is hydrogen or alkyl of 1 to 4 carbon atoms and $R_2$ to $R_7$ are each alkyl with 1 to 6 carbon atoms.

Surprisingly, the indolalhydantoin is soluble in the solvent or mixture of solvents used in the invention. The hydrogenation to skatylhydantoin proceeds in this anhydrous medium without undesired side reactions and only short reaction times are required according to the invention.

The solvents used in the invention correspond to general formulae (I) and/or (II). They can be employed individually or in admixture. The melting point of the solvent or mixture of solvents must appropriately be below 50° C. This requirement in many cases also can be fulfilled by the use of mixtures if one or more of the individual materials to be used has too high a melting point.

In general formula I, $R_1$ to $R_3$ are the same or different. Either each of them signify hydrogen or $R_1$ signifies hydrogen or a straight or branched chain alkyl group with 1 to 6 carbon atoms, usually 1 to 3 carbon atoms, and $R_2$ and $R_3$ each is a straight or branched chain alkyl group with 1 to 8 carbon atoms, preferably with 1 to 6 carbon atoms, or is an aryl, e.g., phenyl group, or $R_2$ and $R_3$ together signify a branched or straight chain alkylene group with 2 to 8 carbon atoms, preferably with 2 to 6 carbon atoms, more usually with 4 to 5 carbon atoms. Or one of the substituents $R_2$ and $R_3$ signifies hydrogen or alkyl of 1 to 6 carbon atoms and $R_1$ and the other of the two substituents $R_2$ and $R_3$ are closed to a straight or branched chain alkylene group with 2 to 8 carbon atoms, preferably with 2 to 6 carbon atoms, more preferably with 3 to 4 carbon atoms. Suitable compounds for example are formamide, N,N-dimethyl formamide, N,N-diethyl formamide, N,N-dimethyl acetamide, N,N-dimethyl propionamide, N-isobutyl formamide, N,N-diisopropyl formamide, N-isoamyl acetamide, N,N-dimethyl butyramide, N-methyl-N-ethyl acetamide, N-formyl piperidine, 1-methyl pyrrolidone, 1,3-dimethyl pyrrolidone or N-methyl formanilide. Other compounds include N,N-dimethyl caproamide, N,N-dimethyl valeramide, N,N-dimethyl pelargonamide, N,N-dimethyl heptylamide, N,N-diisobutyl acetamide, N,N-dibutyl formamide, N-hexyl formamide, N,N-dihexyl formamide, N,N-dihexyl acetamide, N-methyl-N-octyl formamide, N,N-dioctyl formamide, N-formyl pyrrolidine, N-formyl homopiperidine, N-acetyl piperidine, N-butyryl piperidine, N-ethyl formanilide, pyrrolidone, 3-methyl pyrrolidone, 1-ethyl pyrrolidone, N-propyl pyrrolidone.

In general formula II the substituents $R_4$ to $R_7$ are the same or different. Each signifies a straight or branched chain alkyl group with 1 to 8 carbon atoms, preferably with 1 to 6 carbon atoms, usually 1 to 4 carbon atoms, an aryl group, e.g., a phenyl group, an alkylaryl group, e.g., an alkylphenyl group or an aralkyl group, e.g., a benzyl group. Two of the substituents together can also be a straight or branched chain alkylene group with 2 to 8 carbon atoms, preferably with 2 to 6 carbon atoms, usually 4 to 5 carbon atoms. Suitable compounds for example are tetramethyl urea, methyl triethyl urea, N,N-dimethyl-N',N'-diisopropyl urea, N-phenyl-N,N',N'-trimethyl urea, tetraethyl urea or N,N'-dimethyl-N,N'-dibutyl urea. Other compounds include N,N-diethyl-N'N'-dibutyl urea, tetrapropyl urea, tetraisopropyl urea, tetrabutyl urea, trimethyl ethyl urea, N,N'-dimethyl-N,N'-diamyl urea, N,N-diethyl carbamoyl piperidine, N,N-dimethyl carbamoyl pyrrolidine, N,N'-dimethyl-N,N'-dihexyl urea, tetra sec.butyl urea, N,N-diethyl-N',N'-dioctyl urea, trimethyl benzyl urea, trimethyl p-tolyl urea, N,N-diethyl carbamoyl homopiperidine.

As preferred solvents according to the invention there are used N,N-dimethyl formamide, N,N-dimethyl acetamide and/or tetramethyl urea.

The hydrogenation is carried out in the presence of a noble metal catalyst. Preferably there is used elemental metal or metal oxide of the platinum group, especially palladium or palladium dioxide. Other examples of such catalysts include platinum, platinum dioxide, iridium and rhodium. The catalyst also can be added advantageously on a known carrier. For example such catalysts on a carrier include palladium or palladium dioxide on activated carbon, barium sulfate or calcium carbonate. Other carriers include, for example, alumina and silica. Naturally the catalysts can be recovered and used again.

The hydrogenation is carried out at a temperature at which the solvent or mixture of solvents used is present in the liquid state. According to the solvent or mixture of solvents used in general there is employed a temperature between 20° and 180° C.

The hydrogen pressure can be within a wide range. With good, thorough mixing of the liquid and gaseous phase the hydrogenation proceeds at a pressure of for example 3 atmospheres with equally good success as at a pressure of 20 atmospheres and beyond. Thus, for example, the pressure can be from 1 to 100 atm.

Unless otherwise indicated all parts and percentages are by weight.

The process can comprise, consist essentially of or consist of the steps set forth and the materials can comprise, consist essentially of or consist of those set forth.

The invention will be further illustrated by the following examples.

DESCRIPTION OF THE PREFERRED EMBODIMENTS

EXAMPLE 1

A 500 ml agitated autoclave of refined steel (V4A) was charged with 45.4 grams (0.2 mole) of indolalhydantoin, 200 ml of tetramethyl urea and 2.5 grams of catalyst (5% palladium on activated carbon). After flushing with nitrogen there were impressed about 10 atmospheres of hydrogen. The mixture was heated to 80° C and by replacement of the hydrogen taken up the pressure was kept between 3 and 10 atm. After about 2 hours the reaction was finished.

After filtering off the catalyst the main amount of the solvent was distilled off in a vacuum. The residue was stirred with 150 ml of water, whereupon immediate crystallization took place. After filtering with suction, washing with water and drying there was obtained 42.7 grams of pure skatylhydantoin, corresponding to 93.2% of theory. M.P. 220° C.

EXAMPLE 2

The procedure was the same as in Example 1 except that in place of tetramethyl urea there were employed 200 ml of freshly distilled N,N-dimethyl formamide as solvent. The mixture was heated to 100° C at 3 to 10 atm hydrogen pressure. The hydrogenation was finished after about 1 hour. The working up was as in Example 1. Yield 44.1 grams corresponding to 96.3% of theory. M.P. 221° C.

EXAMPLE 3

In a 5 liter agitated autoclave of refined steel (V2A) there were placed 340.5 grams (1.5 moles) of indolalhydantoin, 2 liters of N,N-dimethyl formamide and 25 grams of catalyst (5% palladium on activated carbon) and heated to 110° C under 20 atmospheres hydrogen pressure. Within 50 minutes the take up of hydrogen was complete.

After filtering off the catalyst and distilling off the solvent the skatylhydantoin without further treatment was hydrolyzed under known alkaline conditions, whereby 282.2 grams of D,L-tryptophane were obtained. The yield amounted to 92.4% of theory based on the indolalhydantoin.

EXAMPLE 4

The procedure was the same as in Example 1. There were employed 56.8 grams (0.25 mole) of indolalhydantoin, 200 ml of N,N-dimethyl acetamide and 2.5 grams of catalyst (5% palladium oxide on activated carbon). The hydrogenation took place at 20 atm of hydrogen and at 130° C and was completed after about 35 minutes. After filtering off the catalyst, distilling off the solvent and precipitation by water there were obtained 54.3 grams of skatylhydantoin, corresponding to 94.8% of theory.

EXAMPLE 5

In a 160 liter inner enameled stirred kettle there were placed 6.81 kg (30 moles) of indolalhydantoin, 40 liters of N,N-dimethyl formamide and 500 grams of catalyst (5% palladium on activated carbon). After closing the kettle and flushing with nitrogen it was pressurized with 3 atm of hydrogen. Under stirring it was heated to 100° C whereupon the hydrogen take up already started during the heating up. When the pressure fell below 1.5 atm each time it was repressured to 4 atm of hydrogen. After a total of 40 minutes the hydrogenation was complete. The catalyst was filtered off by a pressure filter and the filtrate concentrated in a vacuum. By precipitation with water there were obtained 6.56 kg (95.5% of theory) of skatylhydantoin.

What is claimed is:

1. A process for the production of skatylhydantoin comprising hydrogenating indolalhydantoin employing a noble metal containing hydrogenation catalyst and a solvent or a mixture of solvents having the formula

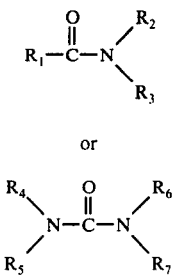

where $R_1$ to $R_3$ are all hydrogen or $R_1$ is hydrogen or 1 to 6 carbon atom alkyl and $R_2$ and $R_3$ are alkyl of 1 to 8 carbon atoms or aryl, or $R_2$ and $R_3$ together are alkylene with 2 to 8 carbon atoms, or one of $R_2$ and $R_3$ is hydrogen or alkyl of 1 to 6 carbon atoms and $R_1$ and the other of $R_2$ and $R_3$ are joined to form an alkylene group with 2 to 8 carbon atoms, and $R_4$ to $R_7$ are alkyl with 1 to 8 carbon atoms, aryl, alkaryl, or aralkyl or two of the substituents $R_4$ to $R_7$ together are alkylene with 2 to 8 carbon atoms, said solvent or mixture of solvents having a melting point below 50° C.

2. A process according to claim 1 wherein $R_1$ to $R_3$ are all hydrogen or $R_1$ is hydrogen or alkyl with 1 to 6 carbon atoms and $R_2$ and $R_3$ are alkyl of 1 to 6 carbon atoms or phenyl or $R_2$ and $R_3$ together are alkylene of 4 to 5 carbon atoms or one of $R_2$ and $R_3$ is hydrogen or alkyl of 1 to 6 carbon atoms and $R_1$ and the other of $R_2$ and $R_3$ are joined to form an alkylene group of 3 to 4 carbon atoms, and $R_4$ to $R_7$ are alkyl of 1 to 6 carbon atoms, phenyl, benzyl, alkylphenyl or two of the substituents $R_4$ to $R_7$ together are alkylene of 4 to 5 carbon atoms.

3. A process according to claim 1 wherein $R_1$ to $R_3$ are all hydrogen or $R_1$ is hydrogen or alkyl with 1 to 3 carbon atoms and $R_2$ and $R_3$ are alkyl with 1 to 6 carbon atoms or $R_2$ and $R_3$ together are alkylene of 5 carbon atoms or one of $R_2$ and $R_3$ is hydrogen or methyl and $R_1$ and the other of $R_2$ and $R_3$ are joined to form an alkylene group of 3 to 4 carbon atoms, $R_4$ to $R_7$ are alkyl of 1 to 6 carbon atoms or one of $R_4$ to $R_7$ is phenyl and the remainder of $R_4$ to $R_7$ are alkyl of 1 to 6 carbon atoms.

4. A process according to claim 1 wherein $R_1$ is hydrogen or alkyl of 1 to 4 carbon atoms and $R_2$ to $R_7$ are each alkyl with 1 to 6 carbon atoms.

5. A process according to claim 4 wherein the solvent is N,N-dimethyl formamide, N,N-dimethyl acetamide or tetramethyl urea.

6. A process according to claim 5 wherein the hydrogenation catalyst is metallic palladium or palladium dioxide.

7. A process according to claim 1 wherein the hydrogenation catalyst is an element of the platinum group of metals or an oxide thereof.

8. A process according to claim 7 wherein the hydrogenation catalyst is metallic palladium or palladium dioxide.

9. A process according to claim 4 wherein the hydrogenation catalyst is on a carrier.

* * * * *